United States Patent [19]

Vrana

[11] 4,421,199
[45] Dec. 20, 1983

[54] SOUND REFLECTOR TYPE HEARING AID

[76] Inventor: Charles K. Vrana, 60 Helen La., Ft. Myers Beach, Fla. 33931

[21] Appl. No.: 354,887

[22] Filed: Mar. 4, 1982

[51] Int. Cl.³ .............................................. G10K 11/10
[52] U.S. Cl. .................................................. 181/136
[58] Field of Search ................. 181/133, 134, 136, 129

[56] References Cited

U.S. PATENT DOCUMENTS

| 656182 | 8/1900 | Ehrhardt | 181/136 |
| 3,618,698 | 11/1971 | McCabe et al. | 181/136 |

Primary Examiner—Benjamin R. Fuller

[57] ABSTRACT

A broad sheet hearing aid of the sound reflecting type having an endless expansion type holding strap inserted in the wings of the device and to also fit over the forehead to hold the device in place.

2 Claims, 1 Drawing Figure

SOUND REFLECTOR TYPE HEARING AID

FIELD OF THE INVENTION

An inexpensive, light weight, broad sheet sound reflector type hearing aid worn behind the head and extending outward from behind the ears to capture and reflect sound vibrations towards the ears to make hearing more effortless and sharper.

ADVANTAGES OF THE INVENTION

Elderly folks complain they can "hear", but sometimes do not get the sound vibrations sharp enough to make out what is said. The present sound reflector type hearing aid corrects this to a degree. It captures, concentrates, and therefore sharpens the sound a few decibels so that it becomes clearer to the listener. This device, although it can be worn in everyday living, is more appreciated when listening to the radio, television, or a hall or open air concert. At the concert, a clear see-through plastic sheet unit will enable the persons sitting behind the wearer to see through the device and experience no obstruction. It also cuts out extraenous noises from the sides and back. The device moves with the head and its light weight wears comfortably.

It likewise improves hearing to those who wear a conventional battery hearing aid because it gathers and reflects the sound to the hearing aid microphone about the ears.

Because of its simple construction, it is obviously inexpensive enough for the poorest person to own. For those who cannot afford the high priced conventional battery hearing aid, this sound reflector hearing aid will be a blessing. One size fits all.

DETAILED DESCRIPTION OF THE DRAWING

Figure 1:
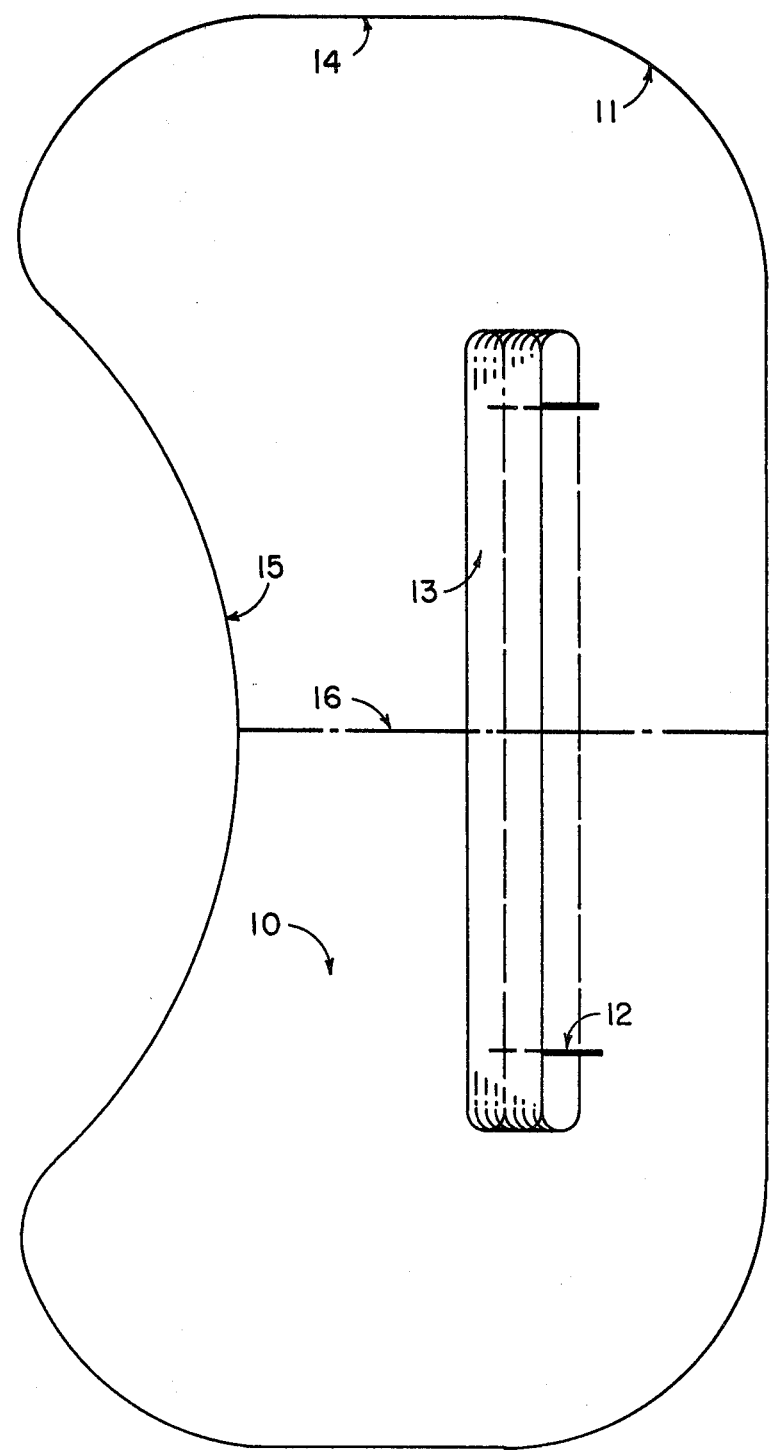
FIG. 1 Showing broad, sound reflective sheet with holding strap in place.

Numeral 10 represents the sound reflector type hearing aid device as a whole. Numeral 11 is a broad sheet of smooth, flexible cardboard or plastic, or a clear, see-through plastic with a sound reflective surface. 12 are the cut slits for the expansion type holding strap 13 to go through, said strap 13 is endless to encircle the head and partially encircle the back of broad sheet 11.

Numeral 14 are sound gathering wing lobes extended outward and downward to catch and reflect sound waves. 15 is a cutaway to give free room for the neck area. In order to save packing space, the Sound Reflector type Hearing Aid folds inward at 16 when not in use.

In use, the Sound Reflector type Hearing Aid is placed around the back of the head with the neck cutaway down, and the expansion holding strap is engaged around the forehead and adjusted for comfort.

What I claim is:

1. An audio sound reflector type hearing aid device comprising a single broad sheet of sound reflecting type material, an endless expansion type holding strap to engage around the head, said holding strap inserted through slots in (a) said single sheet of audio sound reflecting material, said sound reflecting sheet to be positioned around the back of the head, said sound reflecting sheet having a cutaway curve at the lower part of said sound reflector sheet to generally conform with the shape of the neck, said sound reflecting sheet having sound reflecting wings extending outward beyond the ears starting at the approximate point where said endless holding strap enters and leaves said slot in said sound reflector.

2. The device of claim 1, wherein said sound reflecting material is clear, see-through plastic.

* * * * *